United States Patent
Park et al.

(10) Patent No.: US 10,557,259 B2
(45) Date of Patent: Feb. 11, 2020

(54) STERILIZED WATER SPRAY DEVICE AND BIDET SEAT HAVING SAME

(71) Applicant: COWAY CO., LTD., Chungcheongnam-do (KR)

(72) Inventors: Jong-Hyun Park, Seoul (KR); Man-Uk Park, Seoul (KR); Min-Su Song, Seoul (KR); Young-Pyo Kim, Seoul (KR)

(73) Assignee: COWAY CO., LTD., Chungcheongnam-do (KR)

( * ) Notice: Subject to any disclaimer, the term of this patent is extended or adjusted under 35 U.S.C. 154(b) by 0 days.

(21) Appl. No.: 16/086,659

(22) PCT Filed: Feb. 23, 2017

(86) PCT No.: PCT/KR2017/001965
§ 371 (c)(1),
(2) Date: Sep. 20, 2018

(87) PCT Pub. No.: WO2017/164524
PCT Pub. Date: Sep. 28, 2017

(65) Prior Publication Data
US 2019/0071856 A1 Mar. 7, 2019

(30) Foreign Application Priority Data

Mar. 24, 2016 (KR) .................... 10-2016-0035290
Jun. 24, 2016 (KR) .................... 10-2016-0079388

(51) Int. Cl.
| | |
|---|---|
| *E03D 9/08* | (2006.01) |
| *A61L 2/18* | (2006.01) |
| *B05B 3/02* | (2006.01) |
| *A61L 2/22* | (2006.01) |
| *B05B 13/04* | (2006.01) |
| *B05B 1/14* | (2006.01) |
| *A61L 2/26* | (2006.01) |
| *E03D 9/02* | (2006.01) |

(52) U.S. Cl.
CPC ................ *E03D 9/08* (2013.01); *A61L 2/18* (2013.01); *A61L 2/22* (2013.01); *A61L 2/26* (2013.01); *B05B 1/14* (2013.01); *B05B 3/02* (2013.01); *B05B 13/0415* (2013.01); *A61L 2202/15* (2013.01); *E03D 2009/028* (2013.01)

(58) Field of Classification Search
CPC ...................................................... E03D 9/08
USPC ...................................................... 4/443–448
See application file for complete search history.

(56) References Cited

FOREIGN PATENT DOCUMENTS

| JP | H09192542 | 7/1997 |
|---|---|---|
| JP | 2004076298 | 3/2004 |
| KR | 20110105236 | 9/2011 |
| KR | 20120006514 | 9/2012 |

(Continued)

OTHER PUBLICATIONS

International Search Report for PCT/KR2017/001965 dated May 26, 2017, 4 pages.

*Primary Examiner* — Lori L Baker
(74) *Attorney, Agent, or Firm* — Dority & Manning, P.A.

(57) ABSTRACT

Provided is a sterilized water spray device for sterilizing the inner wall of a toilet and a bidet seat having the same. A sterilized water spray device according to the present invention includes: a housing into which sterilized water flows; a tubular nozzle part for spraying the sterilized water flowed into the housing, a through nozzles disposed at one end of the nozzle part, to a toilet; and a driving part for rotating the nozzle part.

11 Claims, 6 Drawing Sheets

(56) References Cited

FOREIGN PATENT DOCUMENTS

| | | |
|---|---|---|
| KR | 101521229 | 5/2015 |
| KR | 101569910 | 11/2015 |
| WO | WO2004028320 | 4/2004 |

STERILIZED WATER SPRAY DEVICE AND BIDET SEAT HAVING SAME

CROSS REFERENCE TO RELATED APPLICATIONS

This application is the U.S. National Stage entry of International Application Number PCT/KR2017/001965 filed under the Patent Cooperation Treaty having a filing date of Feb. 23, 2017, which claims priority to Korean Patent Application Serial Number 10-2016-0035290 having a filing date of Mar. 24, 2016, and Korean Patent Application Serial Number 10-2016-0079388 having a filing date of Jun. 24, 2016, which are incorporated herein by reference.

TECHNICAL FIELD

The present disclosure relates to a sterilized water spraying device to sterilize an inner wall of a toilet, and a bidet seat having the same.

BACKGROUND ART

A toilet is a device upon which a user may sit to relieve him or herself. Recently, toilets with bidets have been used for hygiene. Bidets are devices for cleaning the local parts by spraying water to the local parts of a user, after the user has relieved him or herself. A bidet has an advantage in that the local parts may be kept clean through being washed with water without using toilet paper.

On the other hand, in general, when a toilet is not flushed, portions of relief discharge may adhere to the inner wall of the toilet, and since water is always stored in the toilet, various microorganisms may be present and may proliferate, causing a sanitary problem. Thus, users need to periodically clean toilets by injecting a sterilizing liquid or a cleaning liquid into the inside thereof. In recent years, a bidet equipped with a sterilizing liquid injecting device or a cleaning liquid injecting device has been provided to reduce inconvenience of a user.

However, since a bidet of the related art supplies sterilizing water to a toilet through a fixed cleaning nozzle, it may be difficult to spray sterilizing water as a whole in the inside of the toilet. In addition, even when water pressure is relatively low, it may also be difficult to spray the sterilizing water to a correct position, resulting in a problem in which washing is not properly performed.

DISCLOSURE

Technical Problem

An aspect of the present disclosure is to provide a sterilized water spraying device capable of sterilizing an overall inner wall of a toilet, and a bidet seat having the same.

Technical Solution

According to an aspect of the present disclosure, a sterilized water spraying device includes a housing into which sterilizing water is introduced, a nozzle unit having a tubular shape, configured to spray the sterilizing water introduced into the housing to a toilet through spray holes disposed in one end of the nozzle unit, and a driving unit rotating the nozzle unit.

The sterilized water spraying device may further include a power transmission unit disposed between the driving unit and the nozzle unit, to transmit driving force of the driving unit to the nozzle unit.

The power transmission unit may include a first gear configured to be coupled to the driving unit and rotate, and a gear cylinder disposed to engage with the first gear and to rotate by rotation of the first gear.

The gear cylinder may include a support plate having an arc shape, configured to be coupled to an outer circumferential surface of the nozzle unit, and a second gear disposed on an end of the support plate and coupled to the first gear.

The nozzle unit may be configured in such a manner that the one end of the nozzle unit provided with the spray holes passes through the second gear, to protrude outwardly of the housing.

The housing may include a nozzle accommodating portion having a tubular shape in which the nozzle unit and the support plate are disposed, and the nozzle accommodating portion may be provided with a thread groove formed in an inner circumferential surface of the nozzle accommodating portion, the thread groove being combined with a screw thread screwed thereinto, the screw thread being formed on the other end of the nozzle unit.

The nozzle unit may rotate together with the gear cylinder as the gear cylinder rotates, and simultaneously, may move linearly as the screw thread is screwed into the thread groove.

The sterilizing water may be sprayed in a direction perpendicular to a length direction of the nozzle unit.

According to an aspect of the present disclosure, a sterilized water spraying device includes a housing having a screw thread formed on an inside thereof, a nozzle unit having a tubular shape, having spray holes in one end of the nozzle unit and a screw thread on the other end of the nozzle unit to be screwed into the housing, and a gear cylinder coupled to the nozzle unit to linearly move the nozzle unit.

According to an aspect of the present disclosure, a bidet includes a sterilized water spraying device, a nozzle assembly spraying washing water, and a bidet body provided with the nozzle assembly and the sterilized water spraying device installed thereon.

The sterilized water spraying device may be installed on the bidet body to prevent the nozzle unit from interfering with the toilet when the nozzle unit protrudes.

The sterilized water spraying device may be installed on the bidet body, in such a manner that the nozzle unit is disposed in a region within 80 mm, based on a front end of the bidet body and within 100 mm, based on a central portion of a toilet.

Advantageous Effects

In a sterilized water spraying device, according to an exemplary embodiment, a nozzle may spray sterilizing water onto the interior of a toilet while reciprocating in a linear direction. In addition, spray holes disposed in every direction may rotate and spray sterilizing water. Thus, sterilizing water may be evenly sprayed throughout the interior of the toilet, thereby enhancing sterilizing power in the toilet.

BEST MODE

Hereinafter, exemplary embodiments in the present disclosure will be described with reference to the accompanying drawings. The present disclosure may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity.

Figure 1:
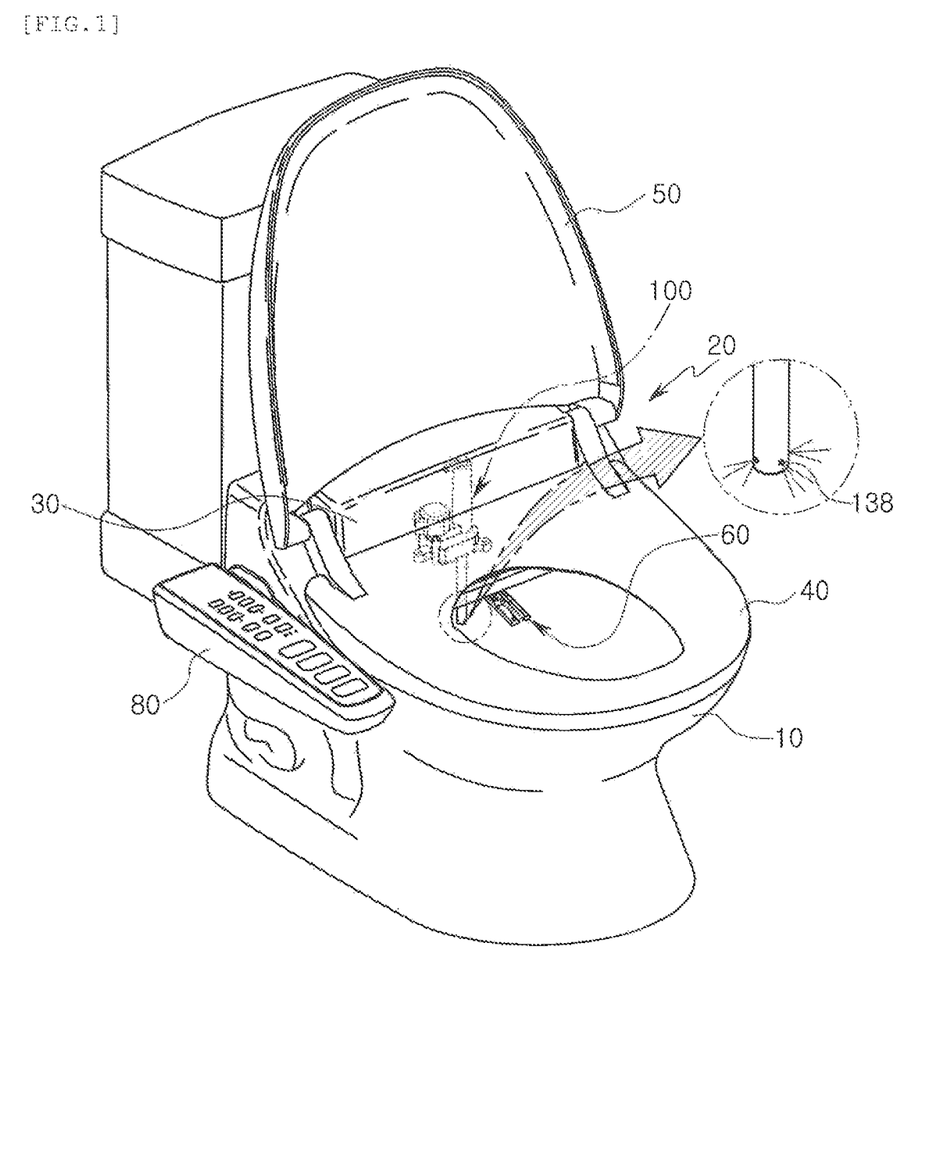
FIG. 1 is a schematic perspective view of a toilet equipped with a sterilized water spraying device according to an exemplary embodiment in the present disclosure.
Figure 2:
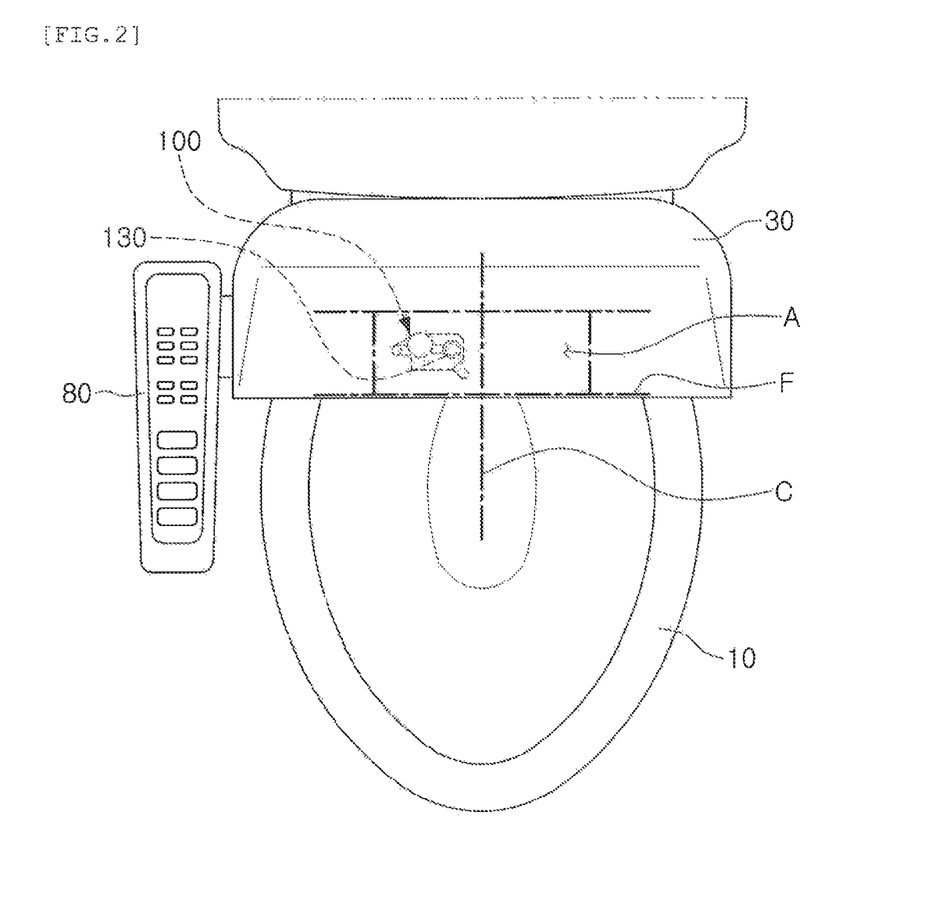
FIG. 2 is a schematic view illustrating a region in which a sterilized water spraying device is disposed in a toilet according to an exemplary embodiment in the present disclosure.

FIG. 1 is a schematic perspective view of a toilet equipped with a sterilized water spraying device according to an exemplary embodiment, and FIG. 2 is a schematic view illustrating a region in which a sterilized water spraying device is disposed in a toilet according to an exemplary embodiment.

Referring to FIGS. 1 and 2, a bidet 20 may be installed on an upper portion of a toilet 10. The bidet 20 may include a bidet body 30, and a toilet seat 40 and a lid 50, and the toilet 40 and the lid 50 may be hinge-coupled to the bidet body 30 to be rotatable. The toilet seat 40 may be formed to have an annular shape so that a user may sit thereupon and may relieve him or herself, and may include a heater therein to heat the toilet seat 40 to an appropriate temperature.

The lid 50 may be formed to have a shape corresponding to the toilet seat 40 to close an open portion of the toilet seat 40 having an annular shape when the toilet 10 is not in use.

A nozzle assembly 60 may be installed inside the bidet body 30. The nozzle assembly 60 may include a cleaning nozzle for the anus and a bidet nozzle for female.

The cleaning nozzle and the bidet nozzle may be respectively installed to be movable forward of the bidet body 30. On front ends of the cleaning nozzle and the bidet nozzle, a nozzle tip having a discharge outlet may respectively be mounted, and cleaning water may be sprayed through the nozzle tip.

In addition, although not illustrated in the drawings, a drying device may be provided inside the bidet body 30. The drying device may be provided with a blowing fan, a blowing duct and a heating device, and may discharge hot air to the front of the bidet body 30.

An operation unit 80 may be provided on one side of the bidet body 30, such that a user may control operations of the bidet 20 through the operation unit 80. For example, when a cleaning button or a bidet button is pressed after a user relieves him or herself, the cleaning nozzle or the bidet nozzle may be moved forward to spray washing water to the local area of a user, and after the washing, hot air may be sprayed by pressing a drying button, to remove moisture from the local area.

In addition, a sterilized water spraying device 100 may be installed in the bidet body 30. The sterilized water spraying device 100 may be a device, receiving sterilizing water supplied by a sterilizing water producing device (not shown), to spray the received sterilizing water to an inner wall of the toilet 10 to sterilize the inner wall of the toilet 10.

The sterilized water spraying device 100 may be mounted on the bidet body 30, in such a manner that a spray hole thereof faces the inner wall of the toilet 10.

In the case of the sterilized water spraying device 100, a nozzle unit 130 may move linearly from the bidet body 30, in a manner similar to a bidet nozzle.

The sterilized water spraying device 100 may be configured in such a manner that a spraying operation thereof may be performed by the operation unit 80. For example, the sterilized water spraying device 100 may be configured, such that a toilet sterilization button is provided on the operation unit 80 and the sterilized water spraying device 100 may spray sterilizing water when a user presses the toilet sterilization button.

The sterilized water spraying device 100 may be disposed on the bidet body 30, to prevent the nozzle unit 130 from interfering with the toilet 10 when the nozzle unit 130 protrudes.

To this end, the sterilized water spraying device 100 may be disposed on the bidet body 30, in such a manner that the nozzle unit 130 may be positioned in a region A within 80 mm, based on a front end F of the bidet body 30, and within 100 mm, based on a central portion C of the bidet body 30. In this case, an outer circumferential surface of the nozzle unit 130 may be located in a specific region, for example, in the region A.

For example, if the nozzle unit 130 is located out of a point of 80 mm from the front end F of the bidet body 30 and 100 mm from the central portion C of the bidet body 30, the nozzle unit 130 may not completely protrude and may interfere with the inner wall of the toilet 10, thereby failing to perform a smooth spraying operation.

Thus, the sterilized water spraying device 100 may be disposed in a specific region, for example, in the region A of the bidet body 30, such that the nozzle unit 130 may be prevented from interfering with the toilet 10 when the nozzle unit 130 protrudes.

Figure 3:
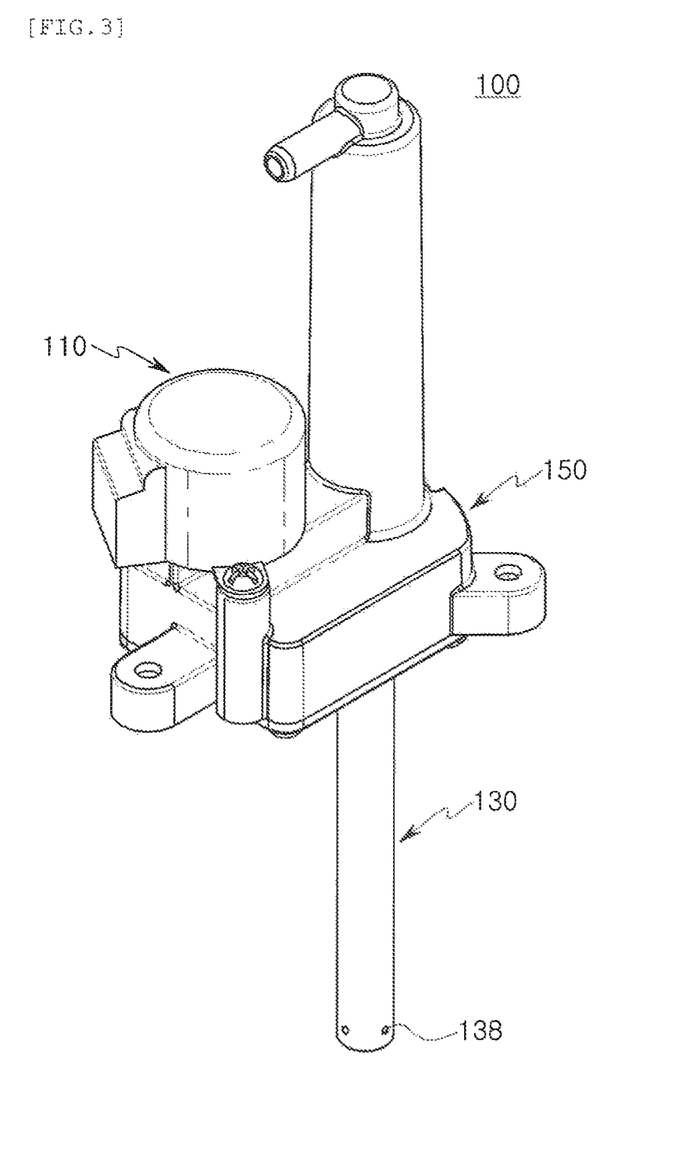
FIGS. 3 and 4 are perspective views schematically illustrating a sterilized water spraying device according to an exemplary embodiment in the present disclosure.
Figure 4:
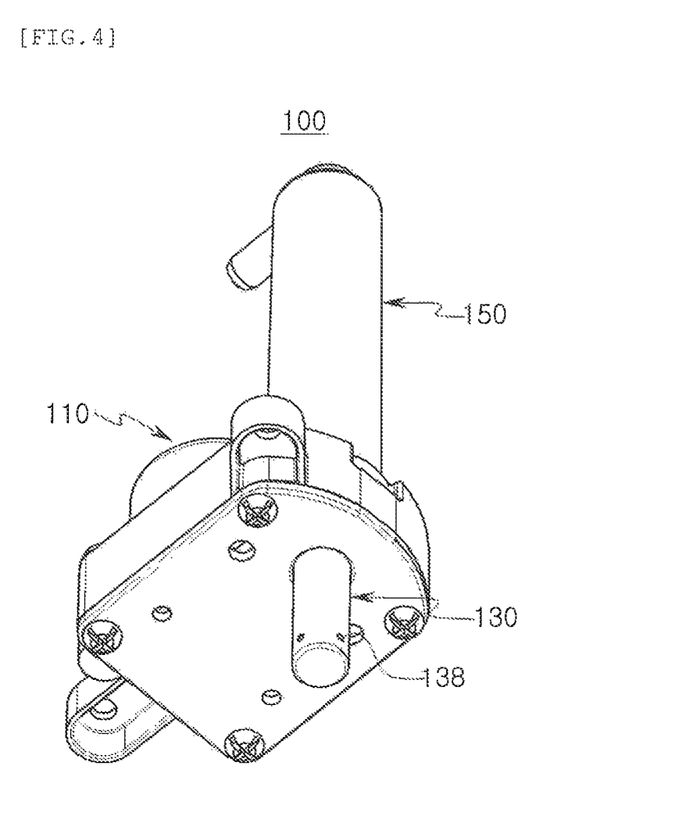
Figure 5:
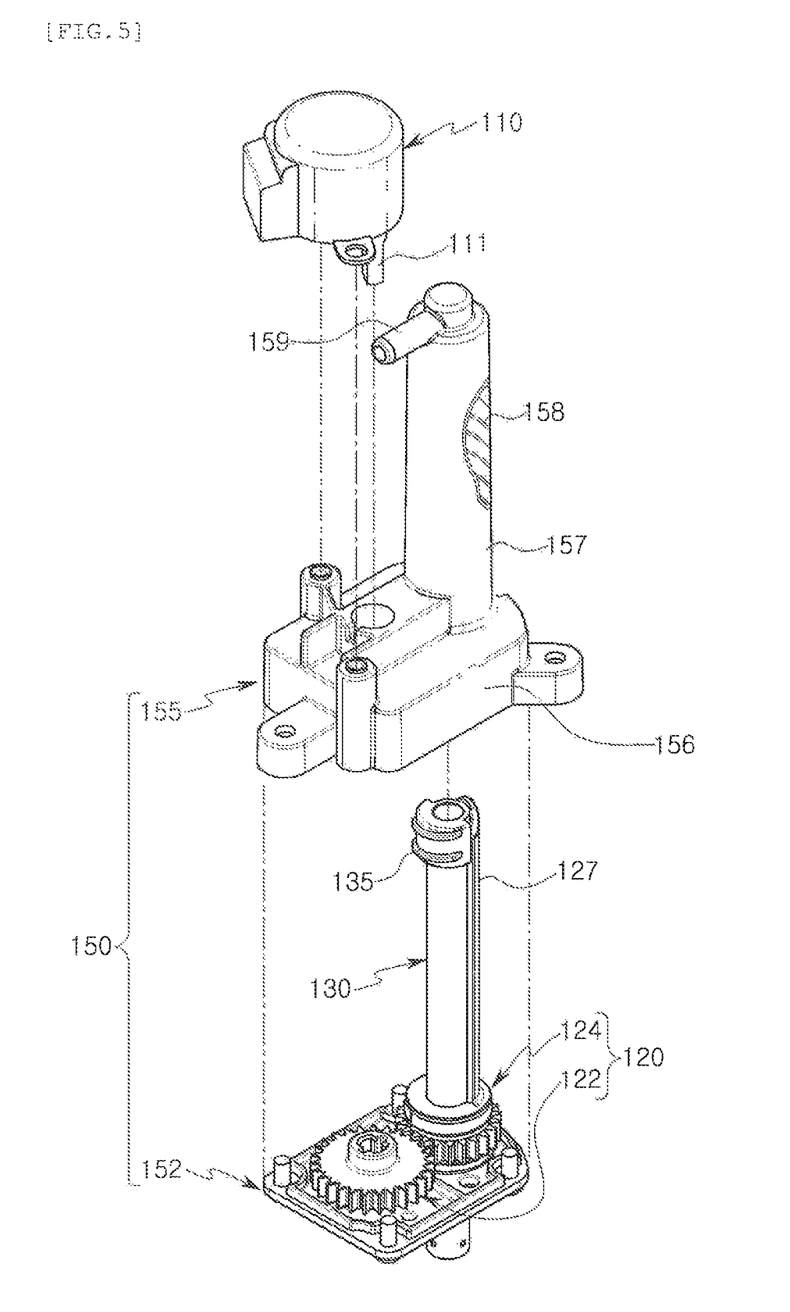
FIGS. 5 and 6 are exploded perspective views of the sterilized water spraying device illustrated in FIG. 3.
Figure 6:
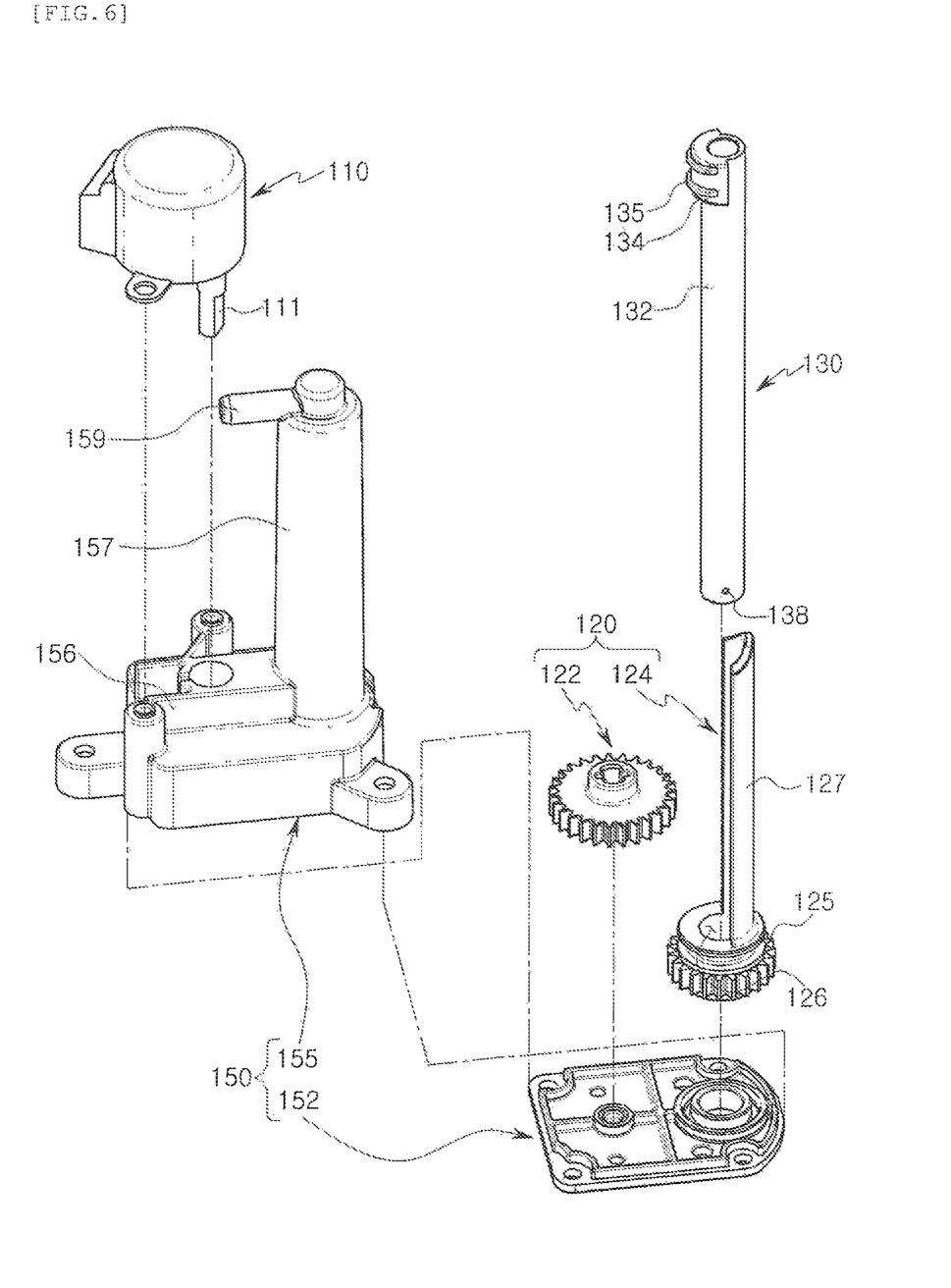

FIGS. 3 and 4 are schematic perspective views of a sterilized water spraying device according to an exemplary embodiment, and FIGS. 5 and 6 are exploded perspective views of the sterilized water spraying device illustrated in FIG. 3. FIG. 3 illustrates a state in which the nozzle unit is protruded to a maximum extent, and FIG. 4 is a bottom perspective view of the sterilized water spraying device, illustrating a state of insertion of the nozzle unit into the housing.

Referring to FIGS. 3 to 6, the sterilized water spraying device 100 according to the exemplary embodiment may be configured to include a driving unit 110, a power transmission unit 120, a nozzle unit 130, and a housing 150.

The driving unit 110 may be provided to rotationally drive and linearly move the nozzle unit 130 to be described later. As the driving unit 110, a power unit such as a motor may be used, but an exemplary embodiment thereof is not limited thereto.

In the exemplary embodiment, the driving unit 110 may be coupled to an exterior of the housing 150, and a rotary shaft 111 may be inserted into the housing 150 to be coupled to a first gear 122, but exemplary embodiments thereof are not limited thereto. The exemplary embodiment thereof may be variously modified, and for example, the driving unit 110 may be disposed inside the housing 150.

The power transmission unit 120 may transmit driving force supplied by the driving unit 110, to the nozzle unit 130.

The power transmission unit 120 may include the first gear 122 and a gear cylinder 124.

The first gear 122 may be disposed inside the housing 150, and may be rotatably coupled to the housing 150. The rotary shaft 111 of the driving unit 110 may be coupled to the center of the first gear 122. Thus, the first gear 122 may rotate together with the rotary shaft 111 of the driving unit 110.

The gear cylinder 124 may be disposed inside the housing 150, and may be rotatably coupled to the housing 150.

The gear cylinder 124 may include a support plate 127 having an arc shape, and a second gear 125 protruding from one end of the support plate 127 in a circumferential direction.

The support plate 127 may be coupled to an outer circumferential surface of the nozzle unit 130 to be described later. An inner circumferential surface of the support plate 127 may be formed of an arc-shaped plate having the same or similar curvature as that of the outer circumferential surface of the nozzle unit 130.

The second gear 125 may be provided with cogwheels formed on an outer circumferential surface thereof, and may be coupled to the housing 150 to be meshed with the first gear 122. Thus, the gear cylinder 124 may be rotated by rotational force of the first gear 122.

A through-hole 126 may be formed in the center of the second gear 125. The nozzle unit 130 may be disposed in the through-hole 126. A diameter of the through-hole 126 may be formed to be greater than an outer diameter of a body portion 132 of the nozzle unit 130.

The nozzle unit 130 may be disposed in the through-hole 126 of the gear cylinder 124, to form a rotation axis of the gear cylinder 124.

The nozzle unit 130 may include a tubular body 132, a spray hole disposed in one end of the body portion 132, and a coupling portion 134 formed on the other end of the body portion 132.

The body portion 132 may be formed to have a circular-shaped pipe form. An outer circumferential surface of the body portion 132 may be in surface-contact with the inner circumferential surface of the support plate 127. Thus, the outer circumferential surface of the body portion 132 may be formed to have a curvature corresponding to a curvature of the inner circumferential surface of the support plate 127.

The coupling portion 134 may protrude from the other end of the body portion 132 in an outer diameter direction, and may be provided with at least one coupling protrusion 135 formed on an outer circumferential surface thereof.

The coupling protrusion 135 may be formed to have the form of a screw thread, to be screwed into a thread groove 158 inside the housing 150 to be described later. Thus, the coupling protrusion 135 may be formed to have a shape and size corresponding to those of the thread groove 158 of the housing 150.

In addition, the coupling portion 134 may be formed to protrude while having a size and shape appropriate to engage with a side surface of the support plate 127 when the nozzle unit 130 is coupled to the gear cylinder 124. Thus, for example, when the gear cylinder 124 rotates, the support plate 127 may support and press the coupling portion 134, and the nozzle unit 130 may rotate together with the gear cylinder 124 thereby.

The spray hole 138 may be provided as a plurality of spray holes disposed in one end of the body portion 132. The exemplary embodiment illustrates a case in which four spray holes 138 are disposed in four directions in the outer diameter direction of the body portion 132 as an example.

Thus, the sterilizing water may be sprayed in a direction perpendicular to a length direction of the body portion 132, but an exemplary embodiment thereof is not limited thereto, and the number and position of the spray holes 138 may be variously modified as required.

The housing 150 may include a first housing 152 constituting a lower portion of the sterilizing water spray device 100, and a second housing 155 disposed on an upper portion of the first housing 152 to be coupled to the first housing 152.

The first housing 152 may constitute a bottom surface of the housing 150. Thus, the first gear 122 and the gear cylinder 124 may be disposed on the first housing 152 to be rotatably coupled to the first housing 152.

One end of the nozzle unit 130 may pass through the second gear 125 of the gear cylinder 124 and the first housing 152, to be disposed outside the housing 150, but may be disposed inside the housing 150 as required.

The second housing 155 may has an internal space, and a bottom surface thereof may be formed in an open form. The first housing 152 may be coupled to the open bottom surface of the second housing 155, thereby completing the housing 150.

The internal space of the second housing 155 may include a gear accommodating portion 156 in which the first gear 122 is accommodated, and a nozzle accommodating portion 157 in which the gear cylinder 124 and the nozzle unit 130 are accommodated.

The nozzle accommodating portion 157 may be formed to have a tubular shape, and may accommodate the nozzle unit 130 and the support plate 127 of the gear cylinder 124 together therein. The thread groove 158 may be formed in an inner wall of the nozzle accommodating portion 157. The coupling protrusion 135 of the nozzle unit 130 may be screwed into the thread groove 158 of the nozzle accommodating portion 157.

Thus, for example, when the support plate 127 of the gear cylinder 124 rotates in the nozzle accommodating portion 157, the nozzle unit 130 may also rotate together with the support plate 127, and simultaneously therewith, may move linearly, outwardly of the housing 150, along the thread groove 158 of the nozzle accommodating portion 157.

A washing water inlet 159 may be formed in one end of the nozzle accommodating portion 157. The washing water inlet 159 may be a passage through which washing water flows into the nozzle accommodating portion 157.

The washing water flowing into the nozzle accommodating portion 157 through the washing water inlet 159 may pass through the inside of the body portion 132 of the nozzle unit 130, to be sprayed externally through the spray hole 138 of the nozzle unit 130.

Subsequently, the operation of the sterilized water spraying device according to the exemplary embodiment will be described.

For example, when a user operates the operation unit 80 to perform a bidet sterilizing function, the driving unit 110 may be driven. Then, the first gear 122 coupled to the driving unit 110 and the gear cylinder 124 engaged with the first gear 122 may rotate together.

The gear cylinder 124 may rotate, using the nozzle unit 130 disposed in the inside thereof, as a rotational axis, and the support plate 127 of the gear cylinder 124 may rotate the nozzle unit 130 while supporting the coupling portion 134 of the nozzle unit 130.

At this time, since the nozzle unit 130 is screwed into the nozzle accommodating portion 157 of the housing 150, the nozzle unit 130 may linearly move as it rotates, to protrude outwardly of the housing 150.

In this process, sterilizing water may be supplied to the interior of the nozzle accommodating portion 157 through the sterilizing water inlet 159 of the housing 150, and may be sprayed externally via the spray holes 138 via the nozzle unit 130.

Thus, the sterilizing water may be continuously sprayed to the inner wall of the toilet through the spray holes 138, in a process in which the nozzle unit 130 rotates and linearly moves.

On the other hand, the return of the nozzle unit 130 may be performed in the reverse of the above-described operation. For example, the first gear 122 may be rotated in a reverse direction through the driving unit 110, thereby moving the nozzle unit 130 to an original position.

As described above, in the sterilized water spraying device according to the exemplary embodiment, a nozzle may spray sterilizing water onto the interior of a toilet while reciprocating in a linear direction. In addition, the spray holes 138 disposed in every direction may rotate and spray sterilizing water. Thus, sterilizing water may be evenly sprayed throughout the interior of the toilet, thereby enhancing sterilizing power in the toilet.

While exemplary embodiments have been shown and described above, it will be apparent to those skilled in the art that modifications and variations could be made without departing from the scope of the present disclosure as defined by the appended claims.

The invention claimed is:

1. A sterilized water spraying device comprising:
a housing into which sterilizing water is introduced;
a nozzle unit having a tubular shape, configured to spray the sterilizing water introduced into the housing to a toilet through spray holes disposed in one end of the nozzle unit; and
a driving unit rotating the nozzle unit; and
a power transmission unit disposed between the driving unit and the nozzle unit, to transmit driving force of the driving unit to the nozzle unit,
wherein the nozzle unit is raised and lowered from the housing by rotating about the central axis of the nozzle unit,
the nozzle unit is rotated when the sterilization water is sprayed.

2. The sterilized water spraying device of claim 1, wherein the power transmission unit comprises:
a first gear configured to be coupled to the driving unit and rotate; and
a gear cylinder disposed to engage with the first gear and to rotate by rotation of the first gear.

3. The sterilized water spraying device of claim 2, wherein the gear cylinder comprises:
a support plate having an arc shape, configured to be coupled to an outer circumferential surface of the nozzle unit; and
a second gear disposed on an end of the support plate and coupled to the first gear.

4. The sterilized water spraying device of claim 3, wherein the nozzle unit is configured in such a manner that the one end of the nozzle unit, provided with the spray holes, passes through the second gear to protrude outwardly of the housing.

5. The sterilized water spraying device of claim 3, wherein the housing comprises a nozzle accommodating portion having a tubular shape in which the nozzle unit and the support plate are disposed, and the nozzle accommodating portion is provided with a thread groove formed in an inner circumferential surface of the nozzle accommodating portion, the thread groove being combined with a screw thread screwed thereinto, the screw thread being formed on the other end of the nozzle unit.

6. The sterilized water spraying device of claim 5, wherein the nozzle unit rotates together with the gear cylinder as the gear cylinder rotates, and simultaneously moves linearly as the screw thread is screwed into the thread groove.

7. The sterilized water spraying device of claim 1, wherein the sterilizing water is sprayed in a direction perpendicular to a length direction of the nozzle unit.

8. A sterilized water spraying device comprising:
a housing having a screw groove formed in an inside thereof;
a nozzle unit having a tubular shape, having spray holes in one end of the nozzle unit and a screw thread on the other end of the nozzle unit to be screwed into the housing; and
a gear cylinder coupled to the nozzle unit to linearly move the nozzle unit.

9. A bidet comprising:
the sterilized water spraying device of claim 1;
a nozzle assembly spraying washing water; and
a bidet body provided with the nozzle assembly and the sterilized water spraying device installed thereon.

10. The bidet of claim 9, wherein the sterilized water spraying device is installed on the bidet body to prevent the nozzle unit from interfering with the toilet when the nozzle unit protrudes.

11. The bidet of claim 10, wherein the sterilized water spraying device is installed on the bidet body, in such a manner that the nozzle unit is disposed in a region within 80 mm, based on a front end of the bidet body and within 100 mm, based on a central portion of a toilet.

* * * * *